(12) United States Patent
Ikeda et al.

(10) Patent No.: US 8,151,396 B2
(45) Date of Patent: Apr. 10, 2012

(54) LIQUID-SAMPLE WIPING MECHANISM AND WIPE-MATERIAL HOLDING MECHANISM FOR OPTICAL MEASUREMENT APPARATUS

(75) Inventors: Eiji Ikeda, Nagaokakyo (JP); Takashi Inoue, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 560 days.

(21) Appl. No.: 12/178,239

(22) Filed: Jul. 23, 2008

(65) Prior Publication Data

US 2009/0025160 A1 Jan. 29, 2009

(30) Foreign Application Priority Data

Jul. 26, 2007 (JP) ................................. 2007-194116
Aug. 2, 2007 (JP) ................................. 2007-201876

(51) Int. Cl.
*G03D 5/06* (2006.01)
*G01N 21/00* (2006.01)
*G01N 1/10* (2006.01)
*B43L 21/00* (2006.01)
*H01L 21/00* (2006.01)
*G01J 3/427* (2006.01)

(52) U.S. Cl. ............ 15/97.1; 15/102; 15/210.1; 422/63; 356/246; 356/319; 356/436; 356/440

(58) Field of Classification Search .................. None
See application file for complete search history.

(56) References Cited

U.S. PATENT DOCUMENTS 3,844,661 A * 10/1974 Birkett et al. ............... 356/414
5,185,531 A 2/1993 Wynn
5,243,409 A 9/1993 Sagner
7,604,997 B2 * 10/2009 Esswein et al. .............. 436/82
2005/0274898 A1 * 12/2005 Watanabe et al. ............ 250/372
2009/0073435 A1 * 3/2009 Tsukuda ...................... 356/319

FOREIGN PATENT DOCUMENTS

JP 51-94880 A 8/1976
JP 55-141054 U 3/1979

(Continued)

OTHER PUBLICATIONS

"NanoDrop ND-1000 Overview," NanoDrop Technologies, LLC, Jul. 24, 2007, Accessed Jul. 18, 2008, http://www.nanodrop.com/nd-1000-overview.html.

(Continued)

*Primary Examiner* — In Suk Bullock
*Assistant Examiner* — Jennifer Wecker
(74) *Attorney, Agent, or Firm* — Sughrue Mion, PLLC

(57) ABSTRACT

After a liquid sample between a sample-holding platform 11 and a window plate 22 is measured, a window plate holder 23 is raised, and a head 14 is moved from a standby position into the gap between the window plate 22 and the sample-holding platform 11. Then, the window plate holder 23 is lowered so as to press the window plate 22 onto the head 14 until the head 14 touches the sample-holding platform 11 below. Then the head 14 is swung back to the original position, whereby a wipe material 40 fitted on the head 14 simultaneously wipes off the liquid sample from both the lower surface of the window plate 22 and the upper surface of the sample-holding platform 11. Pressing the arch springs 35 enables the wipe material 40 to be easily attached to or detached from the head 14.

10 Claims, 6 Drawing Sheets

FOREIGN PATENT DOCUMENTS

| | | | |
|---|---|---|---|
| JP | 54-67986 | U | 5/1979 |
| JP | 05-045273 | A | 2/1993 |
| JP | 5-66546 | U | 9/1993 |
| JP | 07-103897 | A | 4/1995 |
| JP | 09-229847 | A | 9/1997 |
| JP | 10-099246 | A | 4/1998 |
| JP | 11014540 | A * | 1/1999 |
| JP | 2007-170984 | A | 7/2007 |
| WO | 2007/113895 | A1 | 10/2007 |
| WO | WO 2007113895 | A1 * | 10/2007 |

OTHER PUBLICATIONS

Japanese Office Action issued Mar. 1, 2011, in corresponding Japanese Patent Application No. 2007-201876.

Japanese Office Action dated Jul. 5, 2011, issued in corresponding Japanese Patent Application No. 2007-194116.

* cited by examiner

PRIOR ART

000# LIQUID-SAMPLE WIPING MECHANISM AND WIPE-MATERIAL HOLDING MECHANISM FOR OPTICAL MEASUREMENT APPARATUS

The present invention relates to an optical measurement apparatus for delivering light onto a trace liquid sample placed on a sample stage and measuring light transmitted through the sample. More specifically, it relates to a mechanism for wiping off the liquid sample and also a mechanism for holding a wipe material used for wiping off the liquid sample.

BACKGROUND OF THE INVENTION

Measurement of the transmittance, absorbance or other transmission characteristics of a liquid sample by an ultraviolet-visible spectrophotometer or other spectrophotometers generally uses a prism-like or cylindrical cuvette cell holding the liquid sample. However, in the fields of biochemistry in which the quantities of proteins or DNAs need to be determined, the cuvette cell cannot be used because in most cases the quantity of the liquid sample to be analyzed is extremely small.

An example of conventional apparatuses for spectrometric measurement of a trace liquid sample is the ND-1000 Spectrophotometer sold by NanoDrop Technologies, LLC (http://www.nanodrop.com/nd-1000-overview.html, "NanoDrop ND-1000 Overview", NanoDrop Technologies, LLC, Jul. 24, 2007). As shown in FIG. 13, this apparatus (called the "first conventional apparatus" hereinafter) has upper and lower bases 80 and 82 vertically facing each other with a predetermined gap, across which a liquid sample 84 can be held in a vertically expanded form by surface tension. In this state, a light-projecting optical fiber 81 inside the upper base 80 delivers a measurement light into the liquid sample 84. The light transmitted through the sample is received by a light-receiving optical fiber 83 inside the lower base 82. The received light is used to perform a spectrometric analysis or other measurements.

Another conventional example is the "optical measurement instrument for trace liquid sample" disclosed in PCT/JP06/307032 (WO 2007/113895), which is an international patent application filed by Shimadzu Corporation. As shown in FIG. 14, this instrument (called the "second conventional apparatus" hereinafter) includes a disk-shaped rotary sample plate 91 with a plurality of sample-holding portions 92 in the vicinity of its circumference. In a measurement by this apparatus, a liquid sample is initially dropped onto the sample-holding portion 92 at a sample supply position U1. Subsequently, the sample plate 91 is turned until the sample-holding portion 92 reaches a measuring position U2. Then, a transparent window plate 22 is lowered from above to create an optical path of a specific length. In this state, the transmitted light is measured. After the measurement is completed, the window plate 22 is raised, and the sample plate 91 is turned so that the sample-holding portion 92 is moved from the measuring position U2 to a wiping position U3, where the sample liquid is removed by a liquid-absorptive cleaning pad 93. Meanwhile, with the window plate 22 in the raised position, the liquid sample remaining on the lower surface of the window plate 22 is wiped off by a wipe material (which is not shown) separate from the cleaning pad 93.

The first conventional apparatus requires cleaning the end faces of both the light-projecting and light-receiving optical fibers, using a wipe material such as a waste paper, after the measurement of one sample is completed and before the measurement of the next sample is initiated. This cleaning task consumes a considerable amount of time since it is a manual operation to be performed every time the measurement of one sample is completed.

The second conventional apparatus requires complicated mechanisms consisting of a large number of parts for turning the sample plate 91 and cleaning the sample-holding section 92 and window plate 22 with the separate wipe materials.

Another problem of the second conventional apparatus is that the semi-automated sample-wiping mechanism requires the wipe materials to be manually exchanged. Although this job does not need to be performed for every completion of the measurement, the process is rather complicated and consumes considerable time and labor.

The present invention has been developed in view of these problems, and its first objective is to provide a wiping mechanism for quickly and efficiently wiping off a liquid sample in an optical measurement apparatus for a trace liquid sample.

The second objective of the present invention is to provide a wipe-material holding mechanism enabling the wipe material for wiping off a liquid sample to be quickly and easily exchanged in a wiping mechanism for an optical measurement apparatus.

SUMMARY OF THE INVENTION

To solve the aforementioned problems, the present invention provides a wiping mechanism for an optical measurement apparatus for holding a liquid sample between two light-transmission surfaces by narrowing the gap between the two light-transmission surfaces and for measuring light transmitted through the liquid sample. The wiping mechanism includes:

a supporting element having upper and lower surfaces to which a wipe material for wiping off the liquid sample can be attached; and a moving mechanism for moving the supporting element between a position within the gap between the two light-transmission surfaces and a position outside this gap.

The present invention also provides a wipe-material holding mechanism for an optical measurement apparatus for delivering a measurement light onto a liquid sample placed on a sample stage and for measuring light transmitted through the liquid sample. The mechanism is designed for holding a wipe material for wiping off the liquid sample from the sample stage, including:

a supporting element to be fitted into a sleeve-shaped wipe material, the element having a wiping surface at least on one surface; and an elastic part located at least on one side of the supporting element, for holding the wipe material on the supporting element.

The wiping mechanism according to the present invention operates as follows: With the gap between the two light-transmission surfaces widened, the supporting element is inserted into the gap. Then, the two light-transmission surfaces, on which the liquid sample is present, are moved closer to each other until they come in contact with the upper and lower surfaces of the supporting element, respectively. From this state, the supporting element is moved from the gap to the outside, whereby the remaining liquid sample is simultaneously wiped off from both light-transmission surfaces.

The wipe-material holding mechanism according to the present invention allows users to easily attach a sleeve-shaped wipe material to the supporting element or detach it from the supporting element by pressing with their fingers the elastic part provided on the side of the supporting element.

EXPLANATION OF THE NUMERALS

10 . . . Sample Stage
11 . . . Sample-Holding Platform
12 . . . Liquid Sample
13 . . . Base
14, 44 . . . Head
15 . . . Support Pillar
16 . . . Light Source
17 . . . Plane Mirror
18 . . . Condenser Lens
19 . . . Slit
20 . . . Diffraction Grating
21 . . . Detector
22 . . . Window Plate
23 . . . Window Plate Holder
31 . . . Arm
32 . . . Supporting Plate
33, 53A, 53B . . . Rubber Block
34 . . . Rotation Shaft
35 . . . Arch Spring
36 . . . Spring
37 . . . Rail
38 . . . Projection
39 . . . Bend
40 . . . Wipe Material
41 . . . Shaft
42A, 42B . . . Cut
43A . . . Wiping Sheet
43B . . . Sleeve-Shaped Wipe Material

DETAILED DESCRIPTION OF A PREFERRED EMBODIMENT

Figure 1:
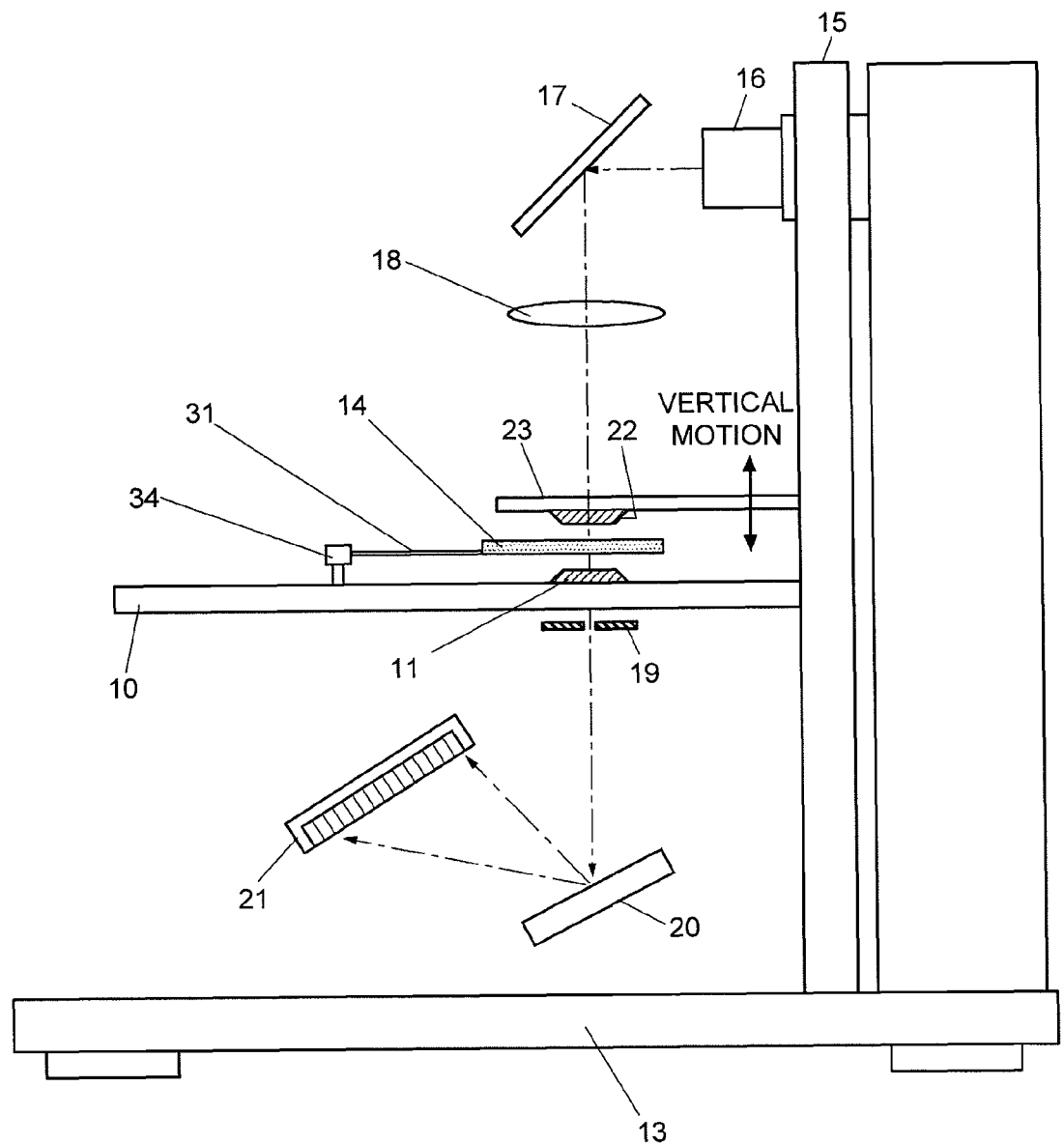
FIG. 1 is a schematic diagram of an optical measurement apparatus for a trace of liquid sample according to an embodiment of the present invention.
Figure 2:
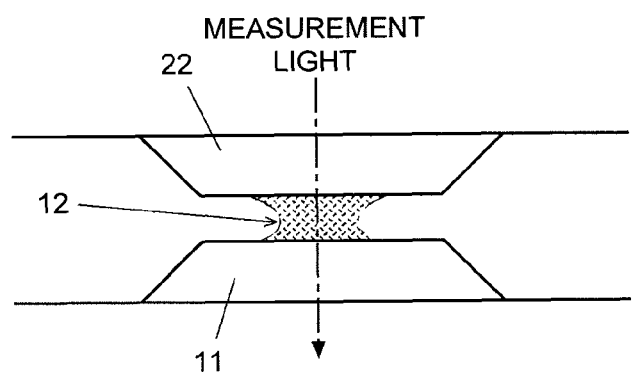
FIG. 2 is a side view of a liquid sample 12 being held in a measurement position.

FIG. 1 is a schematic diagram of an optical measurement apparatus for a trace liquid sample according to the present embodiment. FIG. 2 is a side view of a liquid sample being held in a measurement position.

In FIG. 1, the apparatus has a base 13 on which a vertical support pillar 15 stands, with a substantially horizontal sample stage 10 extending from the middle point of the pillar 15. The sample stage 10 has a hole through which the measurement light can be transmitted. The upper end of this hole is covered with a transparent platform 11 for holding a liquid sample. Located above this sample-holding platform 11 is a window plate holder 23, which can be vertically moved along the pillar 15. The window plate holder 23 also has a transmission hole at a position corresponding to that of the transmission hole of the sample stage 10. The lower end of that hole is covered with a transparent window plate 22, which will hold a liquid sample in conjunction with the sample-holding platform 11.

The light source 16 at the upper portion of the pillar 15 projects a substantially horizontal ray of measurement light onto a plane mirror 17, which reflects the light downward so as to redirect the light to the transmission holes of the window plate holder 23 and sample stage 10.

Located below the transmission hole of the sample stage 10 is a stationary slit 19, under which a diffraction grating 20 is provided. A multi-channel detector 21 is provided at a position where it will receive diffracted light from the diffraction grating 20.

The sample stage 10 is provided with a liquid-sample wiping mechanism including a wipe-material holding mechanism according to the present invention. The liquid-sample wiping mechanism consists of a rotation shaft 34 secured to the sample stage 10, a substantially horizontal swing arm 31 extending from the rotation shaft 34, and a head 14 connected to the end of the arm 31. The level of the head 14 is adjusted so that the head will be positioned immediately above the sample-holding platform 11.

Figure 3:
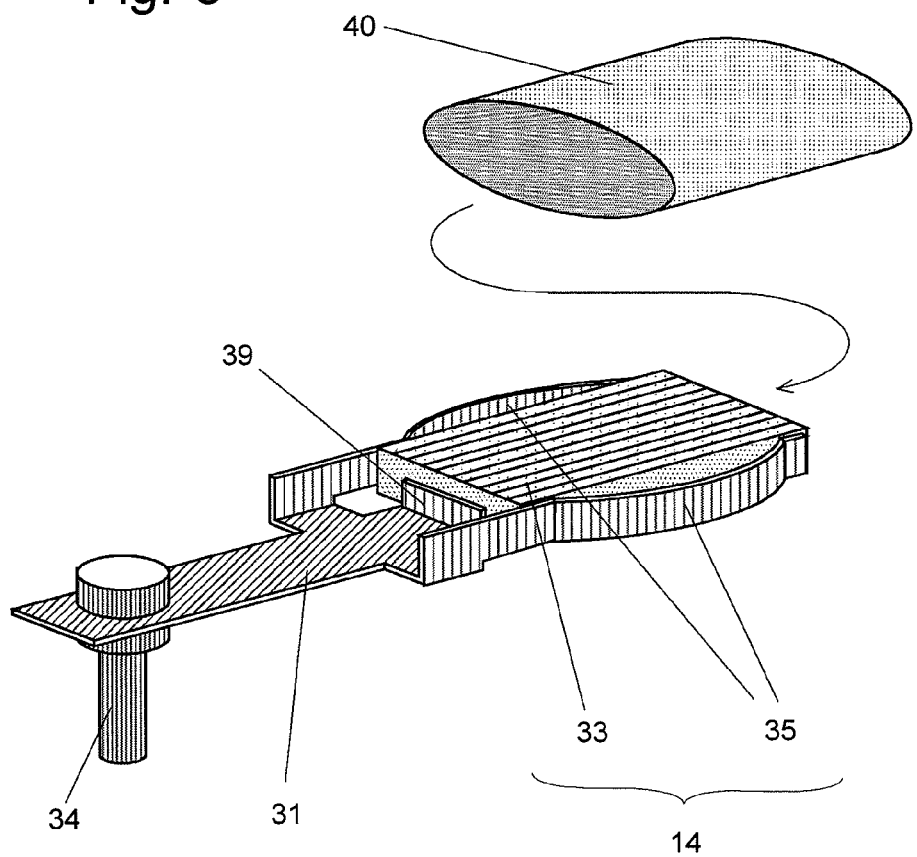
FIG. 3 is a perspective view showing the configuration of a liquid-sample wiping mechanism.
Figure 4:
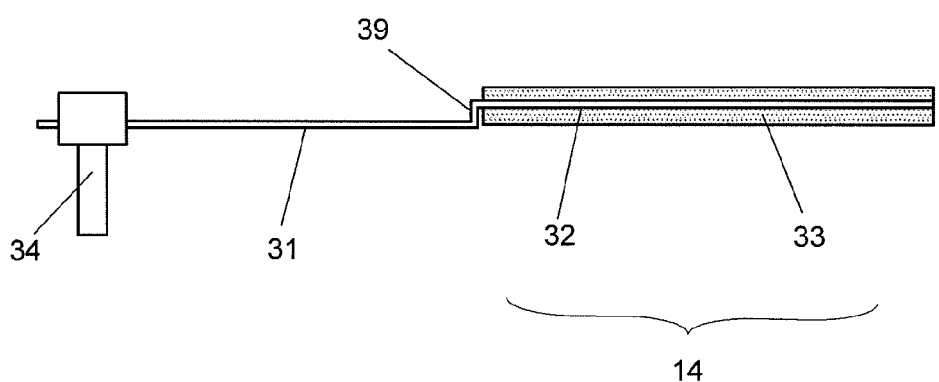
FIG. 4 is a longitudinal sectional view of the liquid-sample wiping mechanism.
Figure 5:
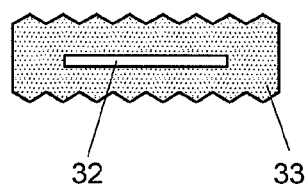
FIG. 5 is an end view of a head 14 shown in FIGS. 3 and 4.

The structure of the liquid-sample wiping mechanism is detailed in FIGS. 3 through 5. As shown in FIG. 3, the head 14 consists of a sleeve-shaped wipe material 40 for wiping off a liquid sample, a rubber block 33 which serves as a core material to be fitted into the wipe material 40, a supporting plate 32 which supports the rubber block 33, and a pair of arch springs 35 on both sides of the supporting plate 32. In the present embodiment, a single piece of sheet metal is used to integrally form the head 14 (the supporting plate 32 with both arch springs 35) and the arm 31.

As shown in FIG. 5, the rubber block 33 is provided with a longitudinally extending central through-hole, into which the supporting plate 32 is inserted to sustain the rubber block 33. The block 33 also has longitudinal ridges on its upper and lower surfaces. These ridges are intended to ensure the wiping effect of the wipe material 40 on the sample-holding platform 11 and the window plate 22. The ridges in FIGS. 3 and 5 are created by cutting straight V-grooves. These grooves may have a different pattern and cross section. For example, they may be wave-shaped grooves with a rectangular cross section.

As shown in FIG. 4, the sheet metal has an intermediate bend portion 39, which defines the borders of the arm 31 (from the fixed end, or the rotation shaft 34, to the bend portion 39) and the supporting plate 32 (from the bend portion 39 to the free end). The bend portion 39 ensures the rubber block 39 to be held at a correct position. It is also possible to replace the single-piece rubber block 33 with two rubber blocks between which the supporting plate 32 is sandwiched.

As shown in FIG. 3, the arch springs 35 each have a base section slightly extending from the side edge of the arm 31 and a spring section extending upward from the base section and then forward. The spring section includes an arched portion, which functions as a spring.

Figure 6A:
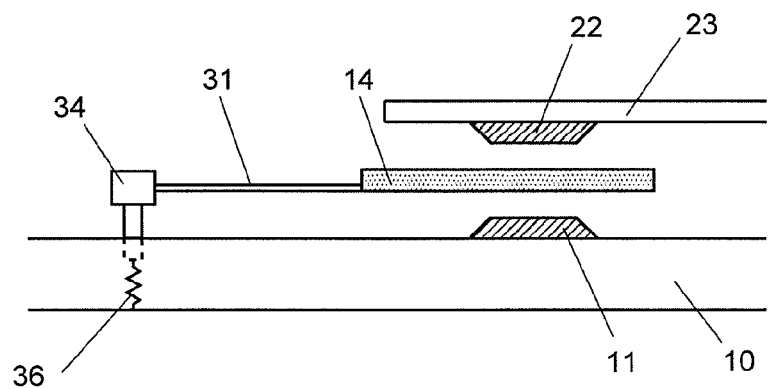
FIGS. 6A and 6B are side views schematically illustrating a vertical motion of a rotation shaft 34 shown in FIGS. 3 and 4.
Figure 6B:
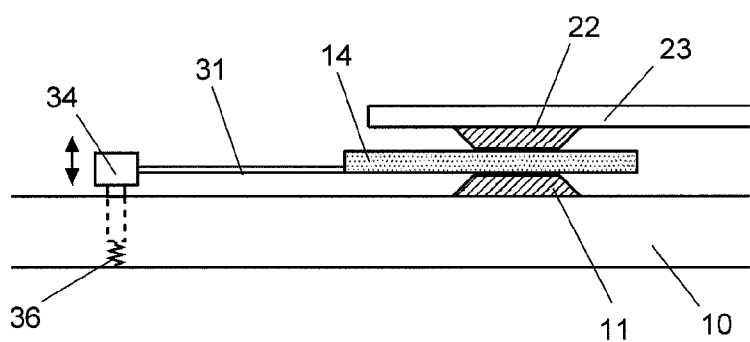
Figure 7A:
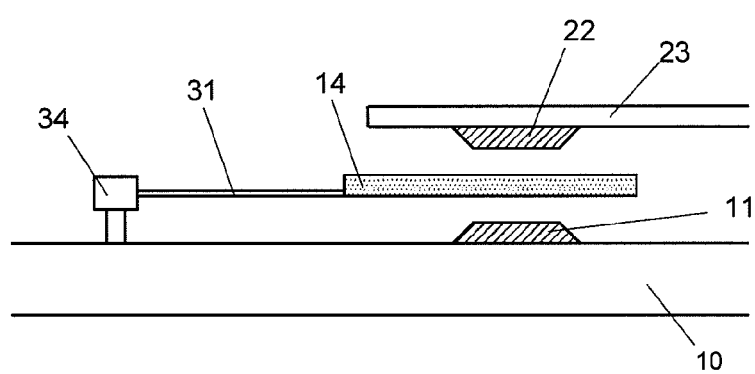
FIGS. 7A and 7B are side views schematically illustrating a vertical deformation of an arm 31 shown in FIGS. 3 and 4.
Figure 7B:
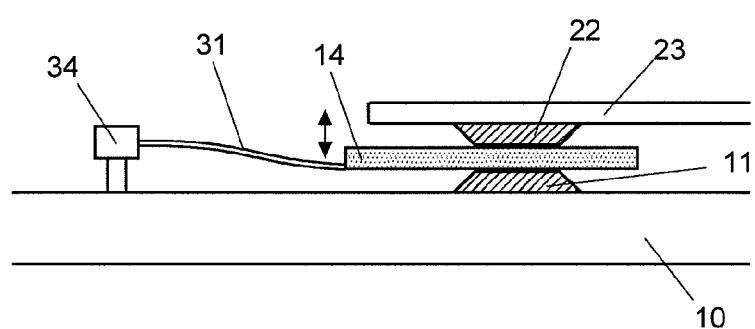

As shown in FIGS. 6A and 6B, the rotation shaft 34 is elastically supported by a spring 36 so that it can vertically move. Therefore, when pressed by the window plate 22, the head 14 will move with the window plate 22 while maintaining its parallel position to the window plate 22 and the sample-holding platform 11. Alternatively, the rigidity of the arm 31 can be reduced so that the head 14 can move with the window plate 22 as shown in FIGS. 7A and 7B.

The sleeve-shaped wipe material 40 can be manufactured by rolling one or plural sheets of thick, water-absorptive waste paper (e.g. paper towel) into a sleeve-like form and then fixing its end with an adhesive or other means. Hot pressing may be used if the waste paper is made from a material that can be thermally adhered.

Measurement of a liquid sample by the optical measurement apparatus of the present embodiment proceeds as follows: With the window plate holder 23 in the raised position, a trace liquid sample is dropped onto the sample-holding platform 11 of the sample stage 10. Then, the window plate holder 23 is lowered until the liquid sample is held between the sample-holding platform 11 and the window plate 22 attached to the holder 23. In this state, the light source 16 is energized to emit measurement light. The emitted light is converged by the condenser lens 18 and passes through the liquid sample held between the sample-holding platform 11 and the window plate 22. After passing through the sample, the light has its cross-sectional area restricted by the slit 19 below. The restricted beam of light falls onto the diffraction grating 20, which disperses the light over a range of wavelengths. The dispersed light illuminates the multi-channel detector 21, which simultaneously detects the intensities of all wavelength components. By processing the detection signals, a spectrometric analysis or other measurements are performed.

After the measurement is completed, the window plate holder 23 is raised, and the liquid sample remaining on the sample-holding platform 11 and window plate 22 is wiped off for the next measurement.

Figure 8A:
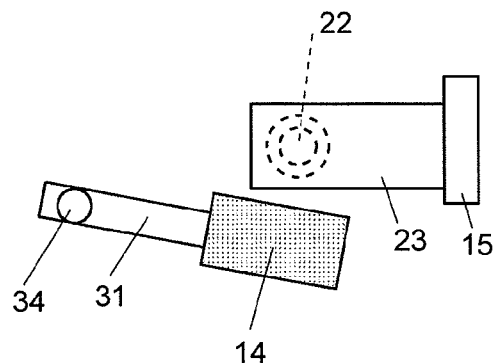
FIGS. 8A and 8B are plan views schematically illustrating a swinging motion of the head 14.
Figure 8B:
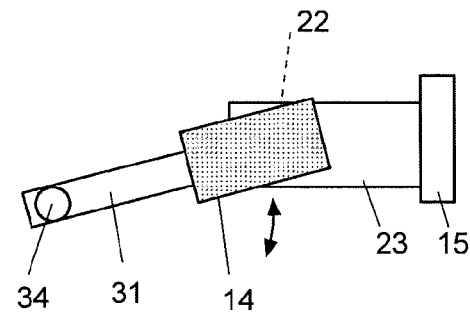

The wiping operation is hereby explained using FIGS. 1, 6 and 8. Initially, the window plate holder 23 is at a position adequately distant from the sample-holding platform 11, as shown in FIG. 1. Then, the head 14, which is usually on standby as shown in FIG. 8A, is swung around the rotation shaft 34 within a plane parallel to the sample stage 10 until the head 14 reaches a position within the gap between the window plate 22 and the sample-holding platform 11, as shown in FIG. 8B. Next, the window plate holder 23 is lowered, pressing the window plate 22 onto the head 14. This pressure makes the rotation shaft 34 move down as shown in FIGS. 6A and 6B, so that the head 14 will eventually touch the sample-holding platform 11 below. From this state, the head 14 is swung back to the position shown in FIG. 8A, whereby the wipe material 40 fitted on the head 14 simultaneously wipes off the liquid sample from both the lower surface of the window plate 22 and the upper surface of the sample-holding platform 11. The swinging motion of the head 14 may be produced by a manual operation or an automatic mechanism using a motor or similar device. In the latter case, it is preferable to automate the entire process by including the motions of the window plate holder 23 and the head 14 into the sample-measuring sequence.

The wipe material 40 should be exchanged every time a predetermined number of measurements have been completed, which may be performed for every measurement if it is necessary. Removal and fitting of the wipe material 40 can be easily done by pressing the arch springs 35 on both sides of the head 14.

Figure 9A:
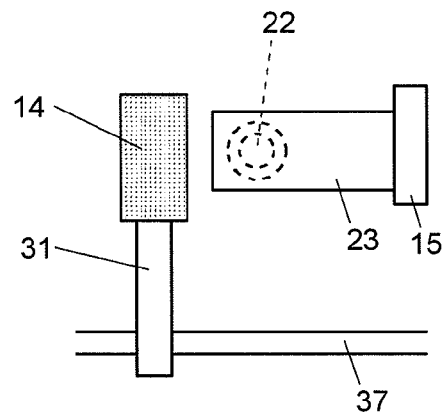
FIGS. 9A and 9B are plan views schematically illustrating a parallel motion of the head 14.
Figure 9B:
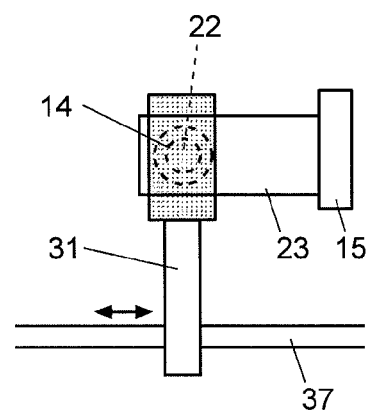
Figure 10A:
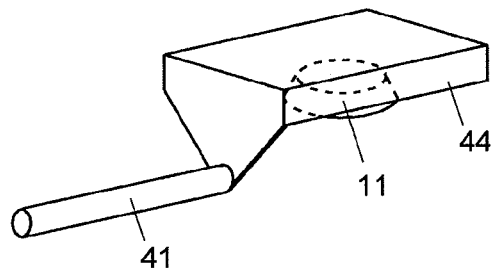
FIGS. 10A and 10B are perspective views schematically illustrating a rotary motion of a head 44 about a horizontal shaft 41.
Figure 10B:
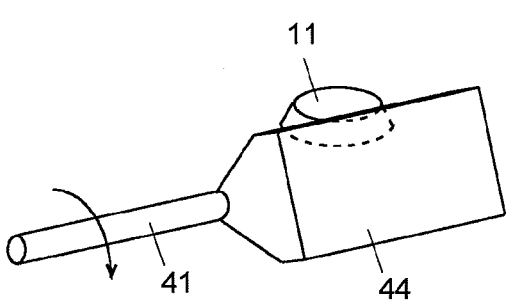
Figure 11:
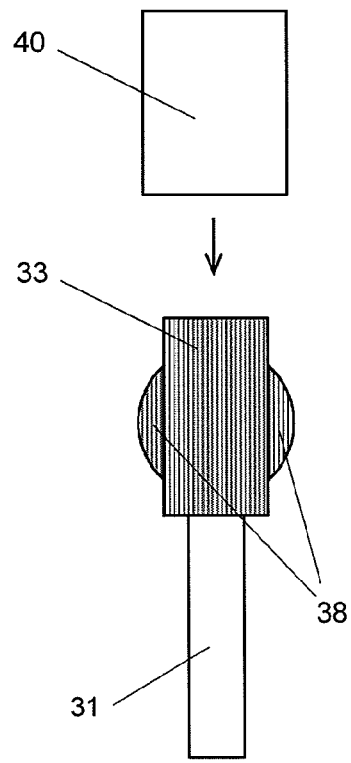
FIG. 11 is a plan view of a liquid-sample wiping mechanism including a rubber block 33 with projections 38 on both sides.

In the previous configuration, the head 14 was swung in parallel with the sample stage 10 so that it would move in parallel with the liquid-holding surfaces of the window plate 22 and sample-holding platform 11. FIGS. 9A and 9B show another configuration, in which the head 14 is translated along a rail 37. In still another configuration shown in FIGS. 10A and 10B, the head 44 is rotated about a shaft 41 parallel to the surface of the sample-holding platform 11. It should be noted that either the window plate 22 or sample-holding platform 11 is omitted from each of FIGS. 9A through 10B; in both of these configurations, the window plate 22 and sample-holding platform 11 can be simultaneously cleaned, as in the configuration with the swing head 14.

As the elastic part for holding the wipe material 40, a projection 38 may be integrally formed with the rubber block 33 on each side of the rubber block 33. It is possible to provide the elastic part only on one side of the rubber block 33, regardless of the type of the elastic part.

Figure 12A:
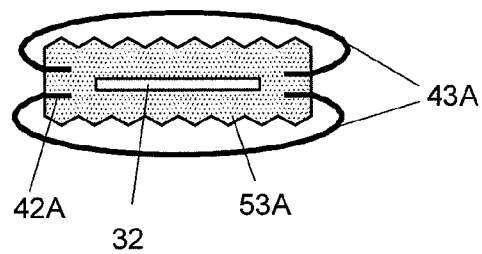
FIG. 12A is an end view of a wiping sheet 43A attached to a rubber block 53A.
Figure 12B:
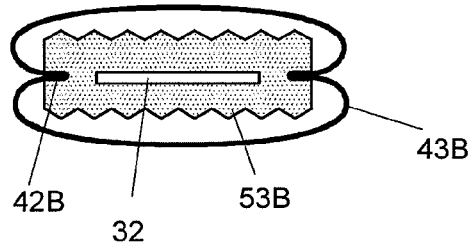
FIG. 12B is an end view of a sleeve-shaped wipe material 43B attached to a rubber block 53B.
Figure 13:
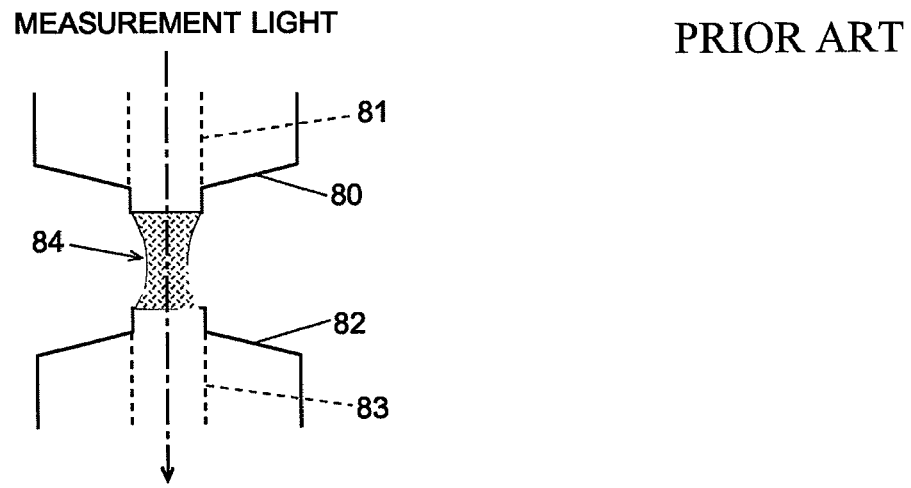
FIG. 13 is a side view of a liquid sample being held in a conventional apparatus for spectrometric measurement of a trace of liquid sample.
Figure 14:
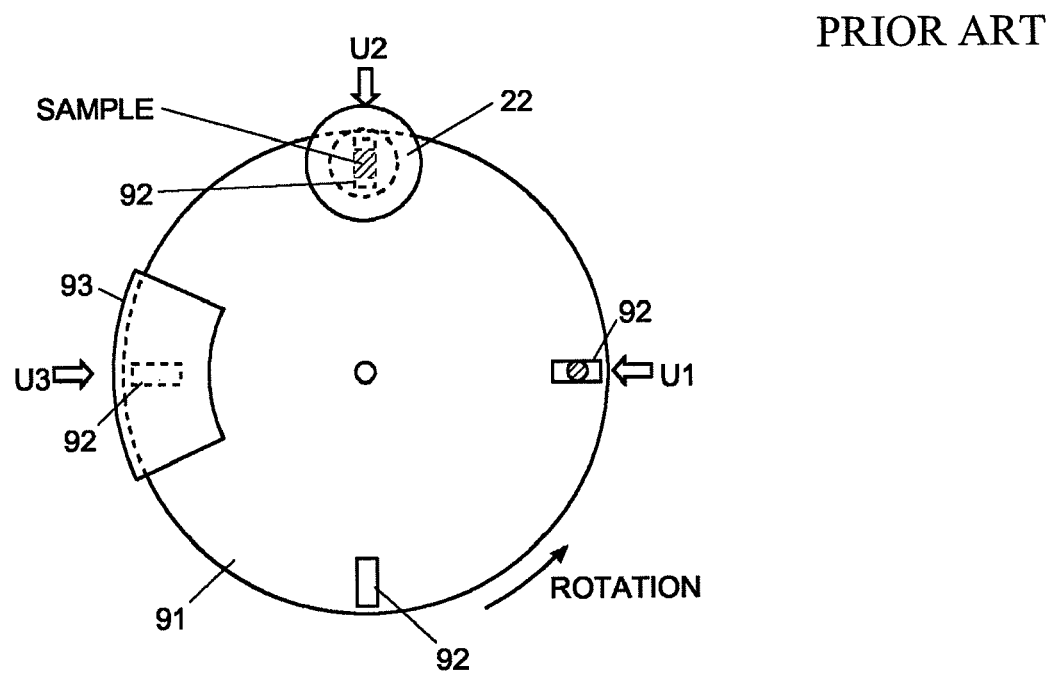
FIG. 14 is a top view of a sample plate of another conventional apparatus for spectrometric measurement of a trace of liquid sample.

In place of the sleeve-shaped wipe material, a wiping sheet may be attached to each of the upper and lower surfaces of the rubber block 33 with a double-stick tape. Alternatively, as shown in FIG. 12A, a pair of wiping sheets 43A may be fixed to a rubber block 53A by tucking the edges of the wiping sheet 43 into the cuts 42A on both sides of the rubber block 53A. Another possible construction is shown in FIG. 12B, in which a portion of a sleeve-shaped wipe material 43B is tucked into the cut 42B on each side of the rubber block 53B. In this case, the side faces of the rubber block 53B function as the elastic part of the present invention.

What is claimed is:

1. A wiping mechanism for an optical measurement apparatus for holding a liquid sample between two light-transmission surfaces by narrowing a gap between the two light-transmission surfaces and for measuring light transmitted through the liquid sample, comprising:
   a supporting element having upper and lower surfaces to which a wipe material for wiping off the liquid sample can be attached;
   a moving mechanism for moving the supporting element between a position within the gap between the two light-transmission surfaces and a position outside this gap; and
   a window plate holder holding one of the two light-transmission surface, moving upward when a measurement is completed and moving downward when the supporting element reaches the position within the gap between the two light-transmission surfaces so that the two light-transmission surfaces come into contact with the upper and lower surfaces of the supporting element, respectively.

2. The wiping mechanism according to claim 1, wherein the moving mechanism swings the supporting element within a plane parallel to the two light-transmission surfaces.

3. The wiping mechanism according to claim 1, wherein the moving mechanism moves the supporting element along a straight line parallel to the two light-transmission surfaces.

4. The wiping mechanism according to claim 1, wherein the moving mechanism rotates the supporting element about a shaft parallel to the two light-transmission surfaces.

5. The wiping mechanism according to claim 1, wherein the supporting element can move vertically when the gap between the two light-transmission surfaces is changed.

6. The wiping mechanism according to claim 1, wherein the wipe material is a waste material used for cleaning.

7. The wiping mechanism according to claim 6, wherein the waste material is sleeve shaped.

8. The wiping mechanism according to claim 7, wherein:
the supporting element is designed to be fitted into the waste material; and
an elastic part for holding the waste material on the supporting element is provided at least on one side of the supporting element.

9. The wiping mechanism according to claim 8, wherein:
the supporting element is a rubber block; and
the elastic part is an arch spring created as an integral portion of a product of sheet metal working including a holder portion for holding the rubber block.

10. The wiping mechanism according to claim 1, wherein a wiping surface of the supporting element is provided with grooves.

* * * * *